(12) United States Patent
Kelly et al.

(10) Patent No.: US 8,061,187 B2
(45) Date of Patent: Nov. 22, 2011

(54) LOSSLESS DROPLET TRANSFER OF DROPLET-BASED MICROFLUIDIC ANALYSIS

(75) Inventors: Ryan T Kelly, West Richland, WA (US); Keqi Tang, Richland, WA (US); Jason S Page, Kennewick, WA (US); Richard D Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 451 days.

(21) Appl. No.: 12/430,490

(22) Filed: Apr. 27, 2009

(65) Prior Publication Data

US 2010/0269573 A1 Oct. 28, 2010

(51) Int. Cl.
*G01N 13/00* (2006.01)

(52) U.S. Cl. ............... 73/61.55; 73/61.56; 73/61.63; 73/64.52; 73/863.23; 73/863.21

(58) Field of Classification Search .............. 73/61.55, 73/61.56, 61.63, 64.52, 863.23, 863.21
See application file for complete search history.

(56) References Cited

U.S. PATENT DOCUMENTS 6,278,111 B1 * 8/2001 Sheehan et al. ............... 250/288
2011/0107822 A1 * 5/2011 Bunner et al. ............... 73/61.52

OTHER PUBLICATIONS

Kennedy, Robert T., et al., "Rapid Electrophoresis in Parallel for High Throughput Analysis" Symposium Abstract, 23rd International Symposium on Microscale Bioseparations, Feb. 1-5, 2009, Boston, MA.
Roman, Gregory T., et al., "Sampling and Eletrophoretic Analysis of Segmented Flow Streams Using Virtual Walls in a Microfluidic Device", Analytical Chemistry, Nov. 1, 2008, 8231-8238 pps., vol. 80, No. 21, ACS Publications, Washington, DC.
Edgar, J. Scott, et al., "Capillary Electrophoresis Separation in the Presence of an Immiscible Boundary for Droplet Analysis," Analytical Chemistry, Analytical Chemistry, Oct. 1, 2006, 6948-6954 pps., vol. 78, No. 19, ACS Publications, Seattle, WA.

* cited by examiner

*Primary Examiner* — Hezron E Williams
*Assistant Examiner* — Rodney T Frank
(74) *Attorney, Agent, or Firm* — Allan C. Tuan

(57) ABSTRACT

A transfer structure for droplet-based microfluidic analysis is characterized by a first conduit containing a first stream having at least one immiscible droplet of aqueous material and a second conduit containing a second stream comprising an aqueous fluid. The interface between the first conduit and the second conduit can define a plurality of apertures, wherein the apertures are sized to prevent exchange of the first and second streams between conduits while allowing lossless transfer of droplets from the first conduit to the second conduit through contact between the first and second streams.

20 Claims, 3 Drawing Sheets

LOSSLESS DROPLET TRANSFER OF DROPLET-BASED MICROFLUIDIC ANALYSIS

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

BACKGROUND

Microfluidics commonly refers to the study, control, and manipulation of fluids within small, enclosed channels having a variety of geometries. Microfluidic devices have proven invaluable for analyzing trace biological and chemical samples because the performance characteristics of analytical separations scale favorably with reduced channel dimensions, and because the integration of sample processing steps with a separation on the same device or "microchip" can be readily achieved. An emerging subfield of microfluidics, referred to as "droplet-based" or "plug-based" microfluidics, involves the encapsulation of aqueous droplets within another immiscible fluid such as an oil. The droplets can be formed uniformly in terms of both size and frequency, and offer the potential to serve as ideal reaction vessels for extremely small samples, including individual biological cells. If an entirely aqueous system were used, the contents that are normally contained in a droplet would diffuse into the surrounding solution, rapidly lowering the concentration of the constituent being detected.

Currently, detection of the contents of droplets typically occurs by passing a droplet through an optical detector, which measures, for example, the fluorescence emitted by a molecule of interest. This detection strategy, and those like it, have severe limitations in that chemical separations are essentially precluded, and only natively fluorescent species or those that have been fluorescently labeled can be detected. As such, only a small number of species can be measured within each droplet. Furthermore, current approaches to transfer droplets from the immiscible fluid to an aqueous one for subsequent separation/analysis typically results in large sample losses and/or require painstaking manipulation of individual droplets using optical trapping techniques. Accordingly, a need exists for methods and apparatuses for rapidly and easily handling samples in droplet-based microfluidic analysis that enables alternative detection approaches, especially those that conserve the content of the droplets and that are compatible with analytical separations prior to detection.

SUMMARY

Aspects of the present invention provide automated and lossless transfer of chemical or biological samples from aqueous droplets into an aqueous stream and can enable alternative detection strategies, especially those that are compatible with analytical separations prior to detection. In one embodiment, a transfer structure for droplet-based microfluidic analysis is characterized by a first conduit containing a first stream having at least one immiscible droplet of aqueous material and a second conduit containing a second stream comprising an aqueous fluid. The interface between the first conduit and the second conduit can define a plurality of apertures, wherein the apertures are sized to prevent exchange of the first and second streams between conduits while allowing lossless transfer of droplets from the first conduit to the second conduit through contact between the first and second streams.

As used herein, aqueous can refer to a liquid that contains water. The aqueous fluid is not limited to only water and can be a mixture of water with another co-solvent, such as methanol or acetonitrile, for example. Accordingly, the contents of an aqueous droplet should be substantially miscible in the second stream, but immiscible in the first stream. An exemplary first stream liquid is an oil.

In one preferred embodiment, the aqueous droplet comprises a single biological cell. For example, the single cell can be trapped within an aqueous droplet that is not much larger than the cell itself and is surrounded by an oil. This configuration can allow for the cell membrane to be ruptured (i.e., lysed), releasing the cellular contents, which can be analyzed after being transferred to the second stream. In another preferred embodiment, the aqueous droplet comprises a fraction of liquid eluted from a liquid chromatography separation.

While the appropriate size of the apertures for successful transfer can depend on fluid dynamics considerations such as flow rate, pressure gradients, viscosities, conduit dimensions, etc., in a particular embodiment, the smallest dimension of each aperture is between 0.02 µm and 20 µm. Aperture sizes need not be uniform, and can vary in size. For example, the apertures can have varying sizes and be arranged in a graduated relationship. In another embodiment, a plurality of apertures can be arranged and sized to compose, in essence, a porous membrane.

In a preferred embodiment, neither the first conduit nor the second conduit is formed from glass. Rather, the conduits can both be formed from elastomers. Furthermore, the conduits would preferably not be altered with a hydrophilic or hydrophobic treatment.

In some embodiments, an electrophoretic separation and/or an electrospray ionization (ESI) operation can occur in the second conduit. In such embodiments, the second conduit can further comprise electrodes applying a capillary electrophoretic (CE) separation and/or an ESI potential in the second conduit. The electrodes can be placed at, or near, each end of the second conduit. In instances employing ESI operations, the second conduit can terminate with an ESI emitter tip directed towards a mass spectrometer. In another configuration that utilizes both ESI and CE separation, an additional channel can merge with the second conduit at an ESI emitter tip to form a liquid junction. A CE separation potential can be applied across the second conduit and an ESI potential can be applied across the additional channel.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DESCRIPTION OF DRAWINGS

Embodiments of the invention are described below with reference to the following accompanying drawings.

DETAILED DESCRIPTION

The following description includes the preferred best mode of one embodiment of the present invention. It will be clear from this description of the invention that the invention is not limited to these illustrated embodiments, but that the invention also includes a variety of modifications and embodiments thereto. Therefore, the present description should be seen as illustrative and not limiting. While the invention is susceptible of various modifications and alternative constructions, it should be understood that there is no intention to limit the invention to the specific form disclosed, but, on the contrary, the invention is to cover all modifications, alternative constructions, and equivalents falling within the spirit and scope of the invention as defined in the claims.

Figure 1:
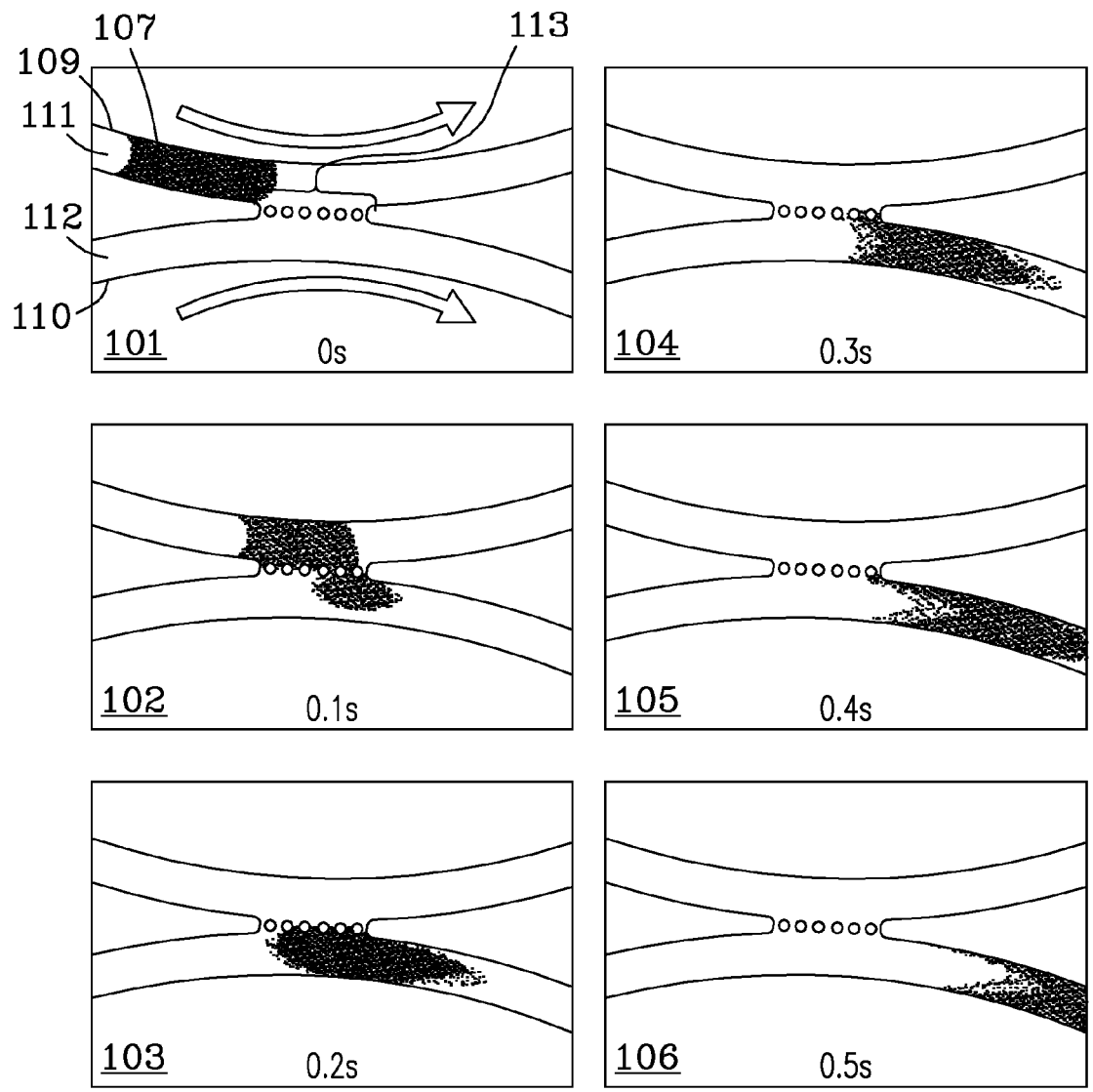
FIG. 1 is an overhead view of one embodiment of the present invention shown at various times during operation.
Figure 2A:
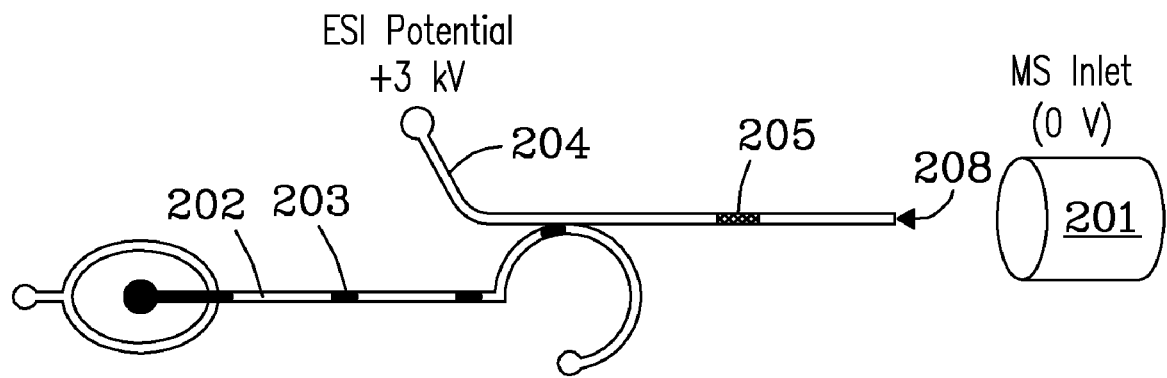
FIGS. 2a and 2b are illustrations depicting two detection strategies enabled by embodiments of the present invention.
Figure 2B:
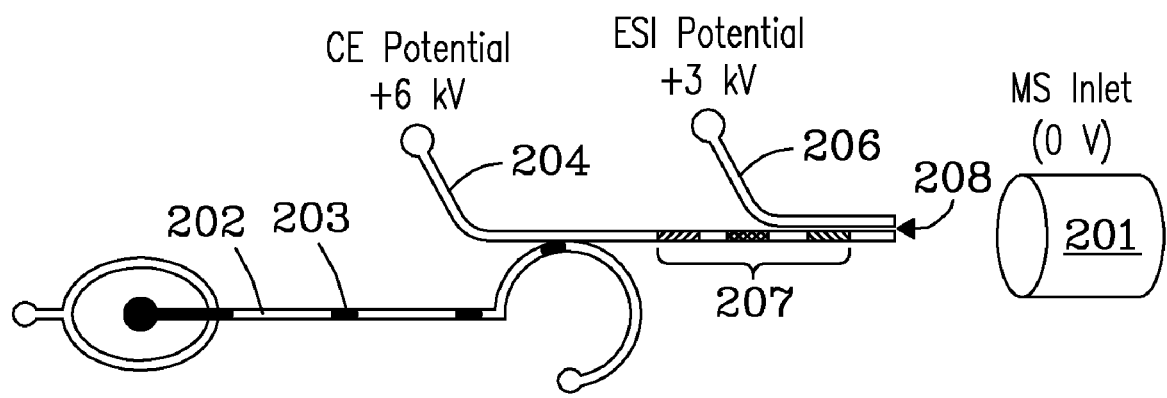
Figure 3:
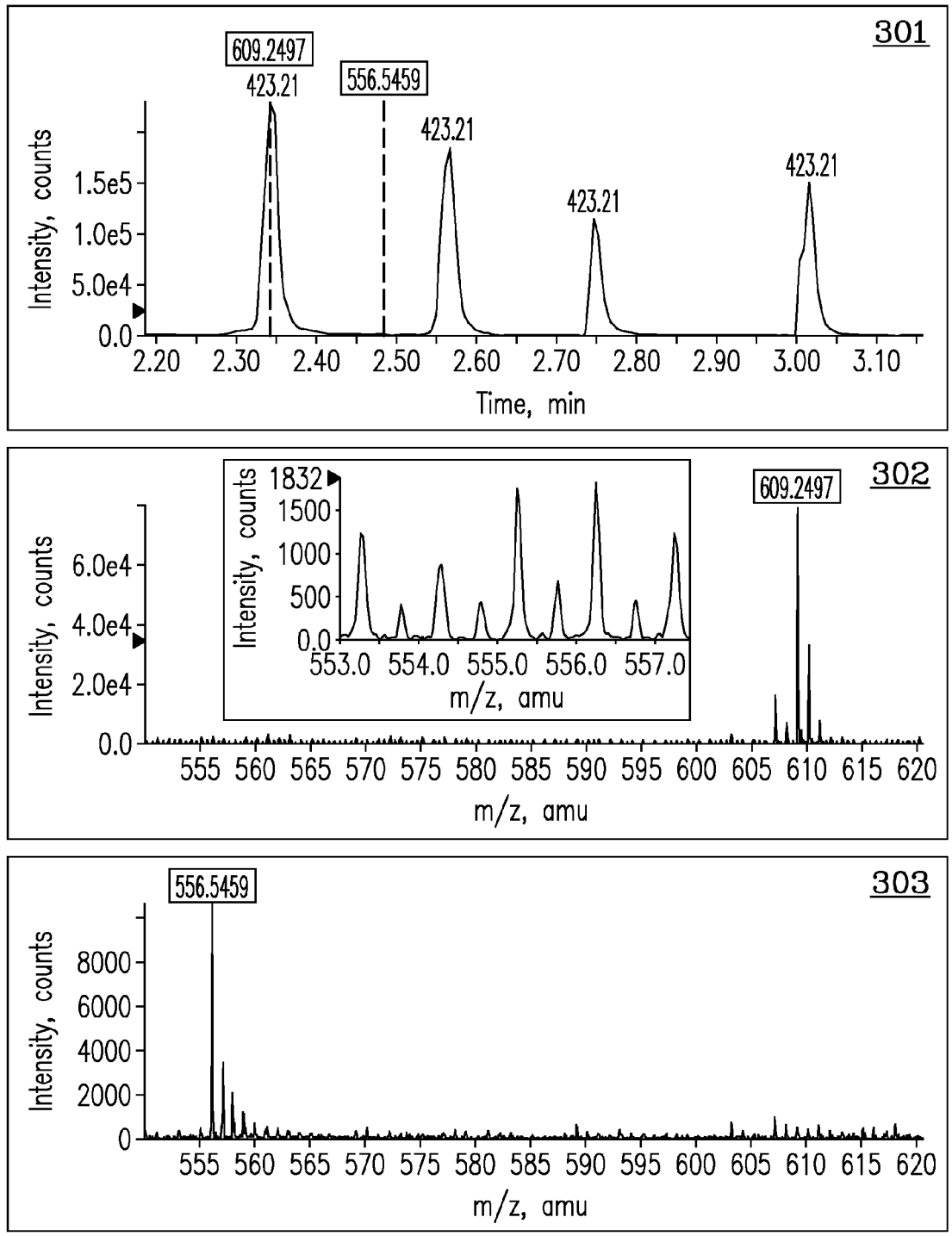
FIG. 3 contains several graphs depicting ESI-MS analysis results after droplet transfer according to embodiments of the present invention.

FIGS. 1-3 show a variety of aspects and/or embodiments of the present invention, which involves bringing a first stream having at least one immiscible droplet of an aqueous material into contact with a second stream that is aqueous. Because the first and second streams are not miscible, they can run parallel to one another without mixing. However, when the aqueous droplet present in the first stream comes in contact with the second aqueous stream, the droplet with its contents rapidly transfers to the aqueous stream. For example, referring to FIG. 1, an overhead view of one embodiment of the present invention is shown at various times during operation as a droplet 107 is transferred from the first conduit 109 to the second conduit 110. Initially 101, the aqueous droplet 107 is encapsulated in an immiscible fluid 111 in the first conduit 109 and is approaching the plurality of apertures 113, which defines an interface between the first and second conduits. At the next moments in time 102-105, as the aqueous droplet passes the interface, the droplet is transferred from the first stream to the second stream. At the final moment in time 106, the droplet has been transferred losslessy to the second aqueous stream.

In the instant example the plurality of apertures 113 defining the interface are formed by a number of posts. And, while seven apertures are shown in FIG. 1, the present invention is not limited by the number of apertures. In practice, the size and number of apertures depends on a number of fluid dynamics considerations including the viscosities of the two streams, the pressure differential, the velocities of the streams and other similar and/or related characteristics. However, surprisingly, a single aperture was unable to withstand even small pressure imbalances between the immiscible streams, such that the boundary between the two streams became unstable and bulk exchange of the immiscible liquids occurred. It is believed, therefore, that a plurality of apertures functions, at least in part, to minimize pressure differentials and/or pressure fluctuations that otherwise result in bulk liquid exchange and/or impede complete transfer in single aperture approaches.

The present invention enables the use of detection techniques that were previously incompatible with droplet-based microfluidics. Referring to FIGS. 2a and 2b, two such strategies are depicted. In FIG. 2a, an aqueous droplet 203 is encapsulated in an immiscible fluid and is contained in a first conduit 202. The second conduit 204 comprises electrodes that can apply a potential for ESI operation. The entire droplet 205 is automatically transferred upon contact with the second conduit and travels in the second conduit 204 to an electrospray emitter 208 positioned in front of the mass spectrometer inlet 201, where the analyte molecules in the transferred droplet 205 can be ionized. Alternatively, referring to FIG. 2b, the electrodes on the second conduit can apply a potential for CE separations. In such an instance, the contents of the transferred droplet 207 can undergo the CE separation prior to arriving at an ESI emitter 208. The additional conduit 206 can have electrodes applying a potential for ESI operation.

As described herein, the present invention provides an efficient and lossless way to create and transfer sample droplets to a stream intended for analysis. Once the aqueous droplet is transferred to the aqueous channel, its contents can be further analyzed by CE followed by ESI-MS, or by ESI-MS alone. Referring to FIG. 3, ESI-MS data from droplets containing 10 µM reserpine are shown. The ESI solvent stream (aqueous) contained 1 µM leucine enkephalin as an internal standard, and the distance from the droplet transfer point to the ESI emitter was 1 mm. Panel 301 is an extracted ion trace showing the transfer of 4 droplets. Panel 302 is a mass spectrum of the droplet contents, which contained reserpine (m/z 609). The inset mass spectrum in 302 showing the absence of leucine enkephalin (m/z 556) indicates that little mixing of the droplet with the aqueous stream occurred upon transfer. In panel 303, a mass spectrum sampled in between droplet transfers shows leucine enkephalin and no reserpine, indicating that there is no detectable carryover of the droplet contents. These results indicate that the present invention is extremely efficient at lossless transfer of droplets and that the resultant droplet maintains plug-like flow. This represents an important improvement over the prior art.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A transfer structure for droplet-based microfluidic analysis characterized by A first conduit containing a first stream having at least one immiscible droplet of an aqueous material;

A second conduit containing a second stream comprising an aqueous fluid; and

An interface between the first conduit and the second conduit that defines a plurality of apertures, wherein the apertures are sized to prevent exchange of the first and second streams between conduits while allowing lossless transfer of droplets from the first conduit to the second conduit through contact between the first and second streams.

2. The transfer structure of claim 1, wherein the apertures have a smallest dimension between 0.02 µm and 20 µm.

3. The transfer structure of claim 1, wherein the conduits are not altered with a hydrophilic or hydrophobic treatment.

4. The transfer structure of claim 1, wherein the apertures vary in size.

5. The transfer structure of claim 4, wherein the apertures of varying sizes are arranged in a graduated relationship.

6. The transfer structure of claim 1, further comprising electrodes applying an electrospray-ionization (ESI) potential in the second conduit, wherein the second conduit terminates with an ESI emitter tip directed towards a mass spectrometer.

7. The transfer structure of claim 1, further comprising an electrode at, or near, each end of the second conduit to apply electric potentials for capillary-electrophoretic (CE) separation, ESI operation, or both.

8. The transfer structure of claim 7, further comprising an additional channel merging with the second conduit at an ESI emitter tip to form a liquid junction, electrodes applying a potential in the additional channel for CE separation, ESI operation, or both.

9. The transfer structure of claim 1, wherein the droplet comprises a single cell.

10. The transfer structure of claim 1, wherein neither the first nor second conduit are formed from glass.

11. The transfer structure of claim 1, wherein the first conduit, the second conduit, or both are elastomers.

12. The transfer structure of claim 1, wherein the plurality of apertures compose a porous membrane.

13. The transfer structure of claim 1, wherein the droplet comprises a fraction of liquid eluted from a liquid chromatography separation.

14. A method for transferring materials in droplet-based microfluidic analytical configurations, the method comprising the steps of:

Flowing a first stream having at least one immiscible droplet of an aqueous material through a first conduit;

Flowing a second stream comprising an aqueous fluid through a second conduit; and Contacting the first stream with the second stream through an interface defined by a plurality of apertures between the first conduit and the second conduit, wherein the apertures are sized to prevent exchange of the first and second streams between conduits while facilitating lossless transfer of droplets from the first conduit to the second conduit.

15. The method of claim 14, further comprising applying potentials to the second conduit for performing ESI.

16. The method of claim 14, further comprising applying different potentials to the second conduit for performing CE separation, ESI operation, or both.

17. The method of claim 14, further comprising applying a potential to the second conduit for performing capillary electrophoresis and applying a potential to a third conduit for electrospray ionization, wherein the second and third conduits terminate in proximity to one another at an ESI emitter tip.

18. The method of claim 14, wherein the droplet comprises a single cell.

19. The method of claim 14, wherein the first conduit, the second conduit, or both are elastomers.

20. The method of claim 14, wherein the droplet comprises a fraction of liquid eluted from a liquid chromatography separation.

* * * * *

UNITED STATES PATENT AND TRADEMARK OFFICE
CERTIFICATE OF CORRECTION

PATENT NO. : 8,061,187 B2
APPLICATION NO. : 12/430490
DATED : November 22, 2011
INVENTOR(S) : Ryan T. Kelly et al.

It is certified that error appears in the above-identified patent and that said Letters Patent is hereby corrected as shown below:

Please correct paragraph 0001 of the application and Column 1, lines 8 through 11 of the issued patent as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Twenty-eighth Day of August, 2012

David J. Kappos
*Director of the United States Patent and Trademark Office*